United States Patent [19]

Brethour

[11] Patent Number: 5,960,105
[45] Date of Patent: Sep. 28, 1999

[54] MEASUREMENT OF INTRAMUSCULAR FAT IN CATTLE

[75] Inventor: John R. Brethour, Hays, Kans.

[73] Assignee: Kansas State University Research Foundation, Manhattan, Kans.

[21] Appl. No.: 08/905,633

[22] Filed: Aug. 4, 1997

Related U.S. Application Data

[63] Continuation of application No. 08/355,912, Dec. 14, 1994, which is a continuation-in-part of application No. 08/058,005, May 3, 1993, Pat. No. 5,398,290.

[51] Int. Cl.$^6$ .............................. G06K 9/00; A61B 8/12; G06F 15/00; A01K 1/00
[52] U.S. Cl. ............... 382/141; 128/660.01; 364/413.25; 364/475; 119/51; 119/52; 382/110
[58] Field of Search ...................................... 382/110, 141; 128/660.01, 660.07; 264/413.25, 475, 567; 119/51, 52

[56] References Cited

U.S. PATENT DOCUMENTS

| | | | |
|---|---|---|---|
| 3,496,764 | 2/1970 | Stouffer | 73/67.8 |
| 3,579,716 | 5/1971 | Stouffer et al. | 17/45 |
| 3,603,303 | 9/1971 | Stouffer | 73/67.8 S |
| 4,099,420 | 7/1978 | Stouffer et al. | 73/629 |
| 4,228,685 | 11/1980 | Wallace et al. | 364/475 |
| 4,288,856 | 9/1981 | Linseth | 364/567 |
| 4,701,745 | 10/1987 | Waterworth | 364/900 |
| 4,785,817 | 11/1988 | Stouffer | 128/660.07 |
| 5,016,009 | 5/1991 | Whiting et al. | 341/67 |
| 5,060,515 | 10/1991 | Kanda et al. | 382/131 |
| 5,140,988 | 8/1992 | Stouffer et al. | 128/660.01 |
| 5,208,747 | 5/1993 | Wilson et al. | 128/660.07 |
| 5,224,175 | 6/1993 | Gouge et al. | 382/128 |
| 5,303,708 | 4/1994 | Stouffer et al. | 128/660.01 |

OTHER PUBLICATIONS

Journal of Animal Science 61:122 (Supp. 1) 1989; #293.
Journal of Animal Science 67:120 (Supp. 1) 1989; #290, #291.

Computer Analysis of Ultrasonic Images for Grading Beef; American Society of Agricultural Engineers; By S.M. Berlow, J.A. Throop, D.J. Aneshansley and J. Stouffer; Dec. 15, 1989.

Enhancement of Analysis of Ultrasound Images of Live Beef; American Society of Agricultural Engineers; By B.R. Thane, B. Park, and A. D. Whittaker; Dec. 15, 1989.

Relationship of Ultrasound Speckle to Marbling Score in cattle; Kansas State University; By J.R. Brethour; Dec., 14, 1989.

Journal of Animal Science 68:240 (Supp. 1) 1990; #33.

Using Ultrasound to Identify Qualitative Traits Such as Marblingl Fort Hays Experiment Station Roundup 1990; KAES Report of Progress No. 59; By J.R. Brethour.

Quality Grade Classification of Beef Carttle by Computer Video Image Analysis of Real–Time Ultrasound Measurements;Texas Technical Agricultural Science & Technology Report; T–5–297 1991; By R.D. Green, T.L. Perkins, K.E. Hamlin and E. B. Fish.

(List continued on next page.)

Primary Examiner—Andrew W. Johns
Assistant Examiner—Monica S. Davis
Attorney, Agent, or Firm—Hovey, Williams, Timmons & Collins

[57] ABSTRACT

A system determines the number of days livestock should be maintained on feed for maximum profit. In the preferred embodiment, current attributes such as marbling and backfat thickness are used to predict what these attributes, as predicted attribute values, will be at various times in the future. These predicted attributes along with other factors such as projected rate of weight gain, costs of feed and livestock prices are used to determine how many days the livestock should be maintained on feed in order to maximize profit.

44 Claims, 7 Drawing Sheets

Microfiche Appendix Included
(1 Microfiche, 52 Pages)

OTHER PUBLICATIONS

Estimating Quality Grade in Cattle With Ultrasound; Fort Hays Experiment Station Roundup 1991; KAES Report of Progress No. 627; By J.R. Brethour.

Journal of Animal Science 70:228 (Supp. 1) 1992; #328.

Progress in Assessing and Predicting Marbling in Live Cattle With Ultrasound; Fort Hays Experiment Station Roundup 1992; KAES Report of Progress No. 653; By J.R. Brethour.

Autocorrelation of Ultrasound Speckle and Its Relationship to beef Marbling; American Society of Agricultural Engineers; by Y. Liu, D.J. Aneshansley and J.R. Stouffer; Summer, 1992.

Journal of Animal Science70:220 (Supp. 1) 1992; #329.

Journal of Animal Science 70:228 (Supp. 1) 1992; #348.

Computer Analysis of Ultrasonic Images of Grading Beef; American Society of Agricultural Engineers; S. M. Berlow et al, Dec. 1989.

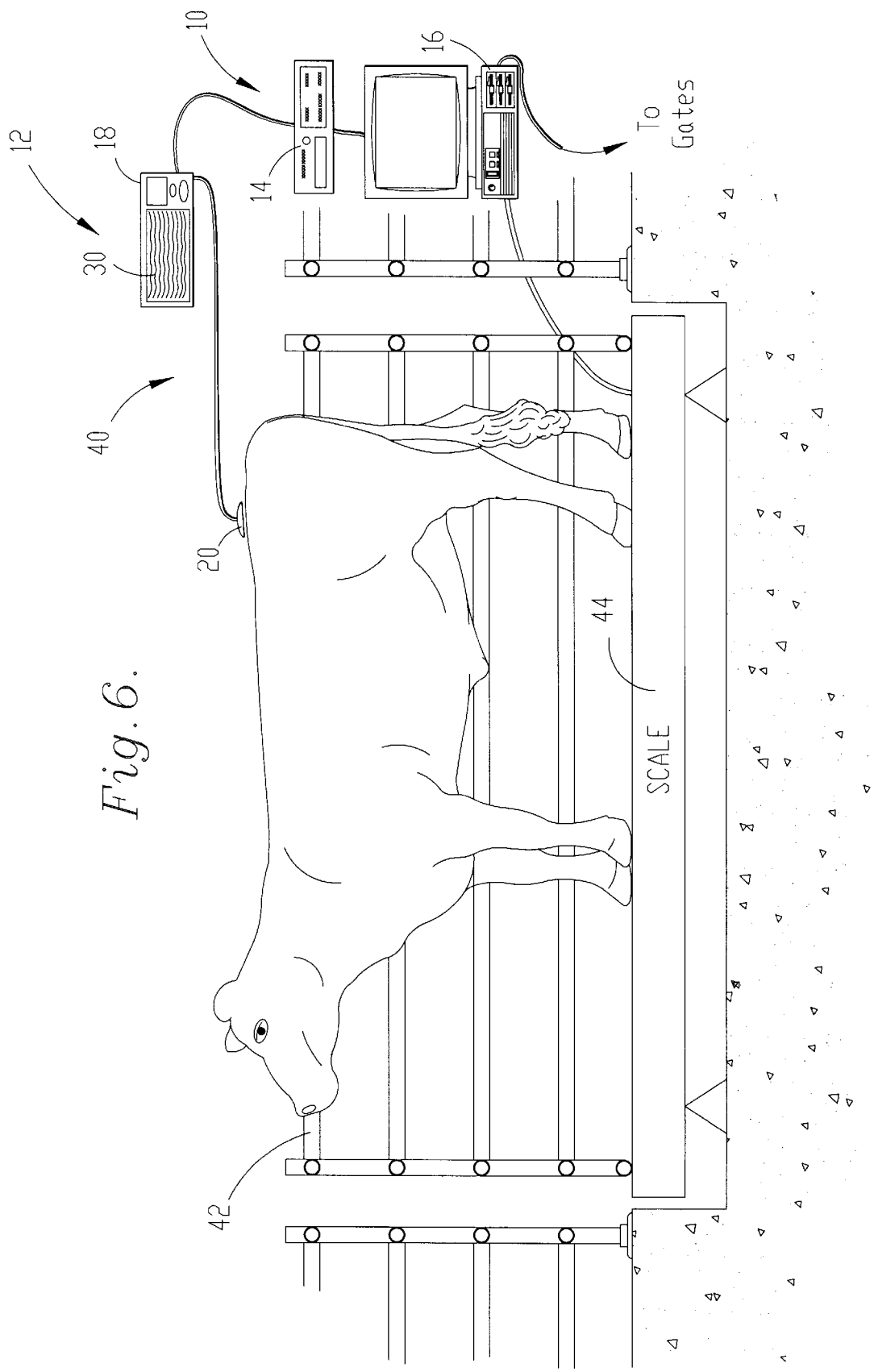

MEASUREMENT OF INTRAMUSCULAR FAT IN CATTLE

This application is a continuation of application number 08/355,912 filed Dec. 14, 1994, now abandoned, which is a continuation-in-part of Ser. No. 08/058,005 filed May 3, 1993, now U.S. Pat. No. 5,398,290.

MICROFICHE APPENDIX

A microfiche appendix containing a source code of a computer program useful in accordance with the present invention is appended hereto as 1 sheet of microfiche containing 52 frames.

BACKGROUND OF THE INVENTION

1. Field of the Invention

The present invention concerns the measurement of intramuscular fat, i.e., marbling, in cattle using ultrasound to produce an image of an interior portion of a muscle and then to analyze data representative of that image to produce a measurement of marbling.

2. Description of the Prior Art

The grading systems for beef carcasses emphasize leanness in terms of yield grades and palatability in terms of quality grades, ice. intramuscular fat or marbling. Marbling is considered an indicator of favorable ogano-leptic properties such as juiciness, flavor and tenderness. The yield and quality grades of beef are determined after slaughter. If these grades could be determined accurately in live cattle, producers would have the ability to cluster live cattle during the feedlot phases on the basis of anticipated grades to satisfy packer and consumer specifications. Additionally, this would enable cattle breeders to select breeding stock on the basis of the desirable grading traits.

Ultrasound techniques have been used with some success for determining anticipated yield grades in cattle. A smooth tissue boundary such as that between subcutaneous fat and muscle results in a specular reflection of the ultrasound that produces a congruent image on the ultrasound monitor. Because of this, ultrasound produces a fairly accurate image of backfat and other attributes predictive of yield grade.

The ultrasound techniques have not been successful, however, in producing images representative of marbling. This is because the intramuscular fat deposits of varying sizes and shapes present discontinuities that cause sound waves to scatter rather than echo back to the ultrasound probe. This scattering causes constructive and destructive interference at the probe in a manner analogous to acoustical noise and produces a graininess or mottling in the ultrasound images known as "speckle." Additionally, as marbling increases, the degree of scatter increases.

In the prior art, various attempts have been made to use the speckle itself as an indicator of marbling. For example, in one prior art technique, the speckle in ultrasound images is analyzed visually. With sufficient experience and training, this technique has provided encouraging results, but requires subjective judgment by an individual; subjective judgment in the grading of beef has been a problem in the prior art because it leads to inconsistent results over time and from individual to individual.

SUMMARY OF THE INVENTION

The present invention solves the prior art problems discussed above and provides a distinct advance in the state of the art. In particular, the system enables the objective measurement of marbling in the muscular tissue of live cattle.

In the preferred embodiment, an ultrasound device is used to produce image data from the muscle tissue in live cattle wherein the image data is in the form of pixels having respective grey levels. The image data is then analyzed in a computer to produce a value or score representative of marbling. In preferred forms, the marbling score is determined as a function of pixel value correlation in a co-occurrence matrix, partial autocorrelation and non-speckle area. Other preferred aspects of the present invention are set forth hereinbelow.

BRIEF DESCRIPTION OF THE DRAWINGS

FIG. 6 is a schematic illustration of the livestock chute of FIG. 5, scale, ultrasound equipment and computer for controlling the gates.

DETAILED DESCRIPTION OF THE PREFERRED EMBODIMENT

Figure 1:
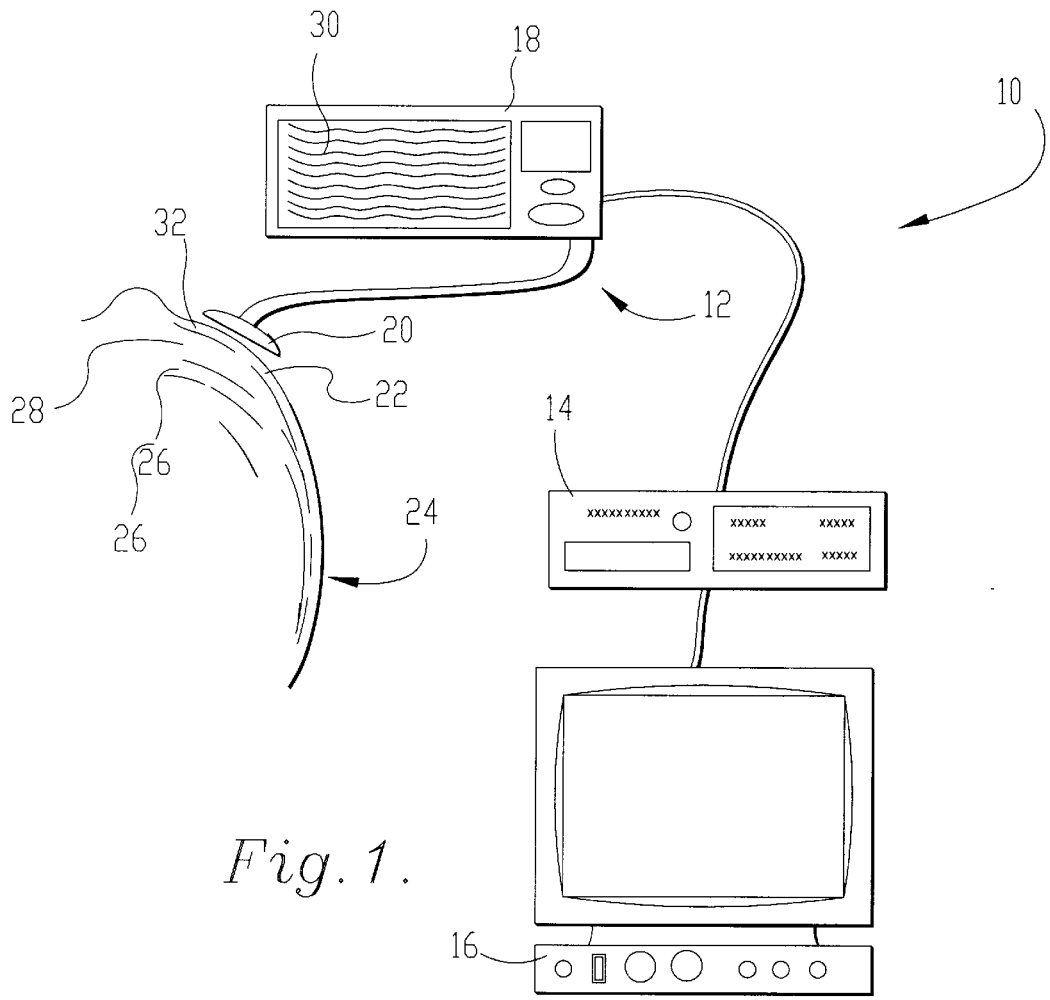
FIG. 1 illustrates the preferred apparatus in accordance with the present invention shown in use.

FIG. 1 illustrates preferred apparatus 10 including ultrasound device 12, video cassette recorder (VCR) 14 and computer 16. Device 12 is preferably Aloka model 210 distributed by Corometrics Medical Systems, Inc., of Wallingford, Conn. operable in real time in the so-called B-mode for producing a two dimensional echogram with pixel brightness indicating signal strength and having a refresh rate of 30 times per second. Images are stored in a four bit format providing 16 levels of grey scale. Device 12 includes signal processor 18 coupled with probe 20 which is preferably Aloka model UST-5021 that operates as a phased array probe with a 3.5 MHz central frequency and a 125 mm window.

VCR 14 is a conventional unit such as a Sharp VC-A5630 or preferably a Sony SLV-757VC coupled with signal processor 18 for receiving and recording about 30 seconds of real time imaging from ultrasound device 12. Computer 16 is preferably a Zenith A-386/25 personal computer equipped with Sony Trinitron monitor. Computer 16 includes a Targa M8 image capture board available from Truevision of Indianapolis, Ind., coupled with VCR 14 for receiving and digitizing images therefrom.

In use, probe 20 is placed on the surface 22 of live stock 24. More particularly, the insonation site is moistened with mineral oil as a couplant between probe 20 and surface 22 to minimize ultrasound attenuation. The preferred probe site is over the twelfth rib 26 beginning at the juncture of the rib and the spinous process at the vertebrae in order to develop a cross sectional image of the longissimus dorsi, i.e., ribeye, muscle 28 near the region where the carcass is to be cut into quarters. In this way, the image is of the same site presented to the grader for marbling classification. The gain of ultrasound device 12 is set at maximum in order to provide an image completely through longissimus muscle 28.

Probe 20 is manipulated laterally so that it follows the curvature of rib 26 until a full tomogram of muscle 28 comes into view on display 30 of signal processor 18, bracketed between backfat layer 32 and rib 26. In preferred practice, it is desired to record about 30 seconds of images from ultrasound device 12 to VCR 14.

Figure 2:
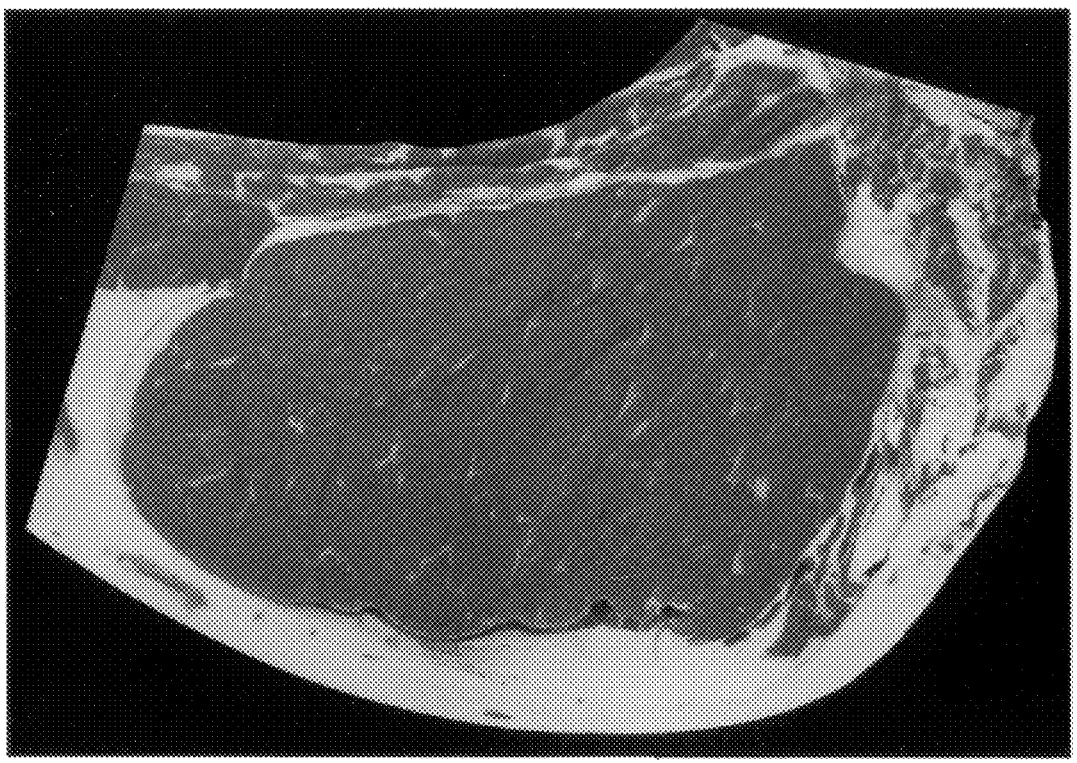
FIG. 2A is a photographic illustration of meat with a grade of USDA Low Select.
FIG. 2B is a photographic illustration of an ultrasonic echogram correlated with a grade of USDA Low Select.
Figure 3A:
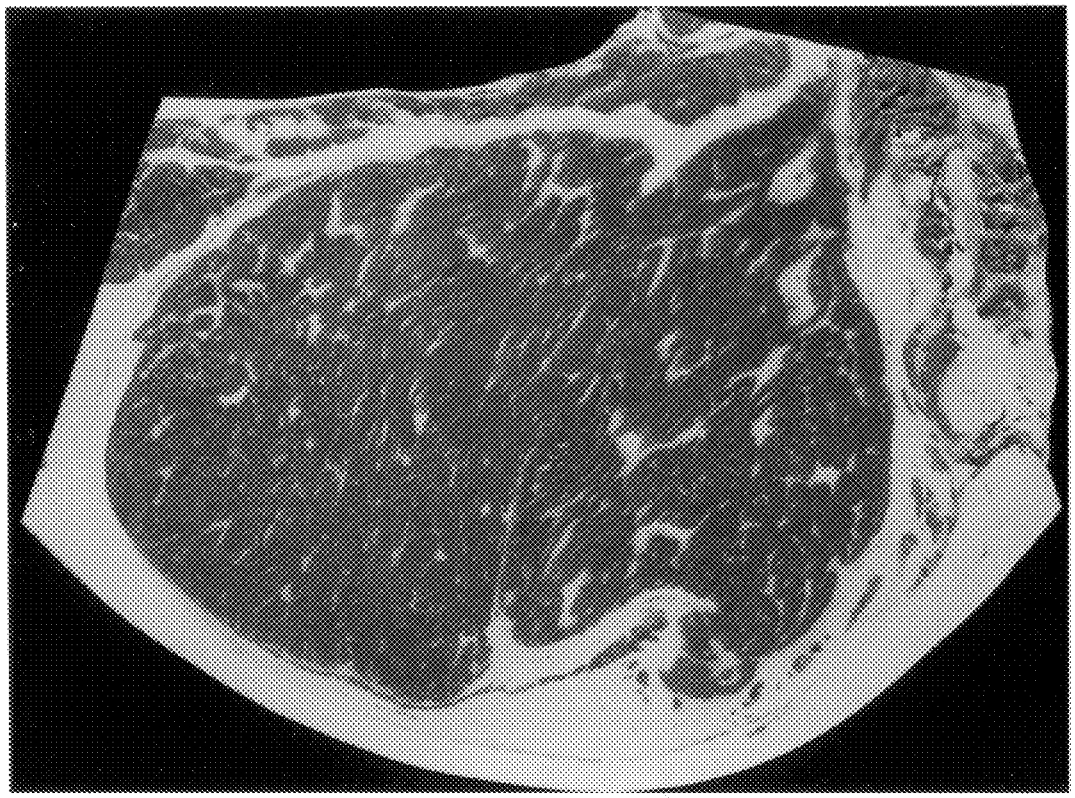
FIG. 3A is a photographic illustration of meat with a grade of USDA High Choice.
Figure 3B:
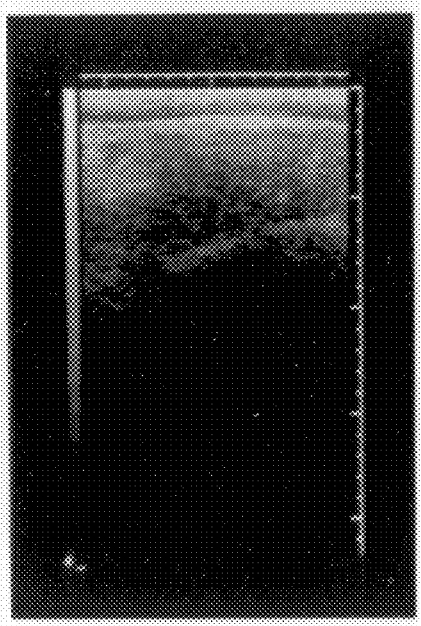
FIG. 3B is a photographic illustration of an ultrasonic echogram correlated with a grade of USDA High Choice.

FIGS. 2B and 3B are photographic illustrations of ultrasonic images produced by device 12 as presented on display 30 and as recorded by VCR 14. As illustrated in these images, and with reference to FIG. 1, the upper layer depicts backfat layer 32 and the curved portion in the lower right of each image shows rib 26 with the area inbetween being muscle 28. As illustrated, the area of muscle 28 shows white patches known as speckle. Intramuscular fat in this area causes random scattering of the ultrasound waves and because of this, the marbling itself is not imaged. Instead, it is the scattering caused by the marbling that results in signal noise that is imaged as the white patches in the area of muscle 28 in FIGS. 2B and 3B. A comparison of these two figures illustrates that the higher level of marbling in FIG. 3D produces the higher level of signal noise known as "speckle" in the region near backfat layer 32.

After the image recordation process is complete as described above, three to five representative frames are selected, digitized and stored in computer 16 as image data representative of the ultrasound image as pixels with eight bits defining 256 grey level values. Ultrasound device 12, however, only portrays 16 grey levels and the digitizer maps these values to eight bits. Computer 16 includes Java video analysis software available from Jandel Scientific of Cote Madera, Calif., which is used to manipulate the computer monitor cursor for outlining and defining a selected region-of-interest of about 3 to 4 cm square presenting a resolution of about 27 pixels per centimeter of tissue with about 8,000 to 10,000 pixels total in the region.

The region-of-interest is selected to be centered between backfat layer 32 and rib 26 within muscle 28, and to present a uniform pattern while avoiding acoustical shadows. The region-of-interest is located in the sector of the longissimus that is distal from the midline of the animal because that area is more likely to present a more consistent pattern of speckle and random specular echoes. The image data of the region-of-interest of each captured frame are processed for the statistical features which are then averaged for further analysis. The image data are initially stored as a TIF file and then converted to an ASCII format so that the data is amenable to image analysis. The pixel values in the stored array are initially preprocessed by using statistical regression to adjust for signal attenuation remaining after gain compensation adjustments of the ultrasound signal processor 12.

Figure 4A:
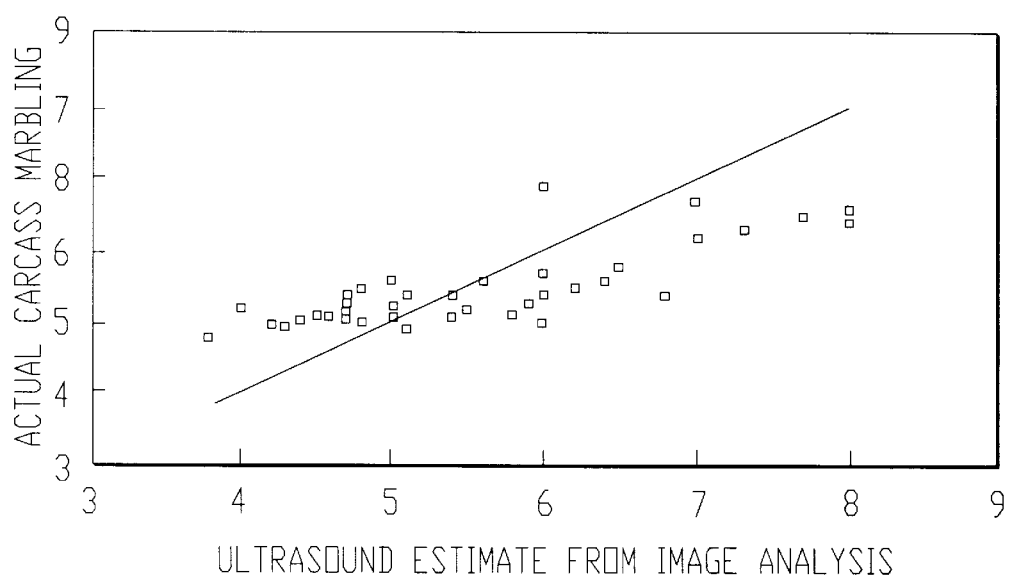
FIG. 4A is a graph representing acores of actual carcass marbling verses marbling scores using visual interpretation of ultrasound images.

As those skilled in the art will appreciate, a vast array of mathematical techniques are available for analyzing images. In the development of the present invention about 500 different techniques were investigated. For example, it was found that conventional first order statistics such as mean pixel values as well as the second, third and fourth moments of those values were insufficient. As a result, second order statistics are used to evaluate the relationships among the pixel gray level values of the region-of-interest, primarily involving co-occurrence and run-length matrices. None of the standard procedures were found to be adequate for measuring intramuscular fat. FIG. 4A illustrates actual marbling scores with those determined using visual analysis of ultrasound images.

Accordingly three variables were developed for building a multiple regression model. These image texture variables include partial autocorrelation, correlation in a co-occurrence matrix and nonspeckle area. These were calculate along pixel vectors that were in the dimension axial to beam transmission. Appendix I incorporated as part of the disclosure hereof illustrates the preferred program written in Fortran for analyzing the image data in computer 16.

The partial autocorrelation variable is a time series analysis used to analyze the pixel grey level values along a row in the time domains. More particularly, the preferred partial autocorrelation is the regression of a pixel value with the pixel value two steps behind it, independent of the values of the intervening pixels. This is obtained from a formula involving two autocorrelations of a pixel with the pixel at lag 1 and lag 2. The specific formula is:

$$AR2.1=(AR2-AR1^2)/(1-AR1^2)$$

where AR2.1 is the partial autocorrelation of the grey level value on the pixel at lag 2 independent of the pixel at lag 1, AR2 is the autocorrelation of lag 2 and lag 0, and AR1 is the autocorrelation of lag 1 and lag 0.

The data are normalized to a mean of 0 so that the autocorrelation values are the same as autoregressions. This was performed on values in an eight bit format and across all rows as if they were one continuous vector. The values are negative and usually in the range of −0.65 to −0.75 with the values nearest 0 associated with the higher level of marbling.

For the correlation variables a co-occurrence matrix is built by mapping a pixel value (grey level) with that of a neighbor at a designated distances that is, from row vectors across the data set and with eight bit formatting. The matrix is made symmetrical by placing values both above and below the diagonal. The correlation statistic is calculated from the regression of matrix values to the column (or row) values so that a high correlation indicates a predominance along the trace (diagonal) of the matrix and measures the similarity of a pixel value with its designated neighbor. A high co-occurrence correlation is associated with a high degree of marbling and relates to an image with uniform visual texture.

The nonspeckle area variable measures the lack of speckle in the image and is inversely related to marbling. This variable is developed from the run length grey level matrix by assessing the length of runs of the same grey level value along a row in the matrix. Initially the pixel grey level values are mapped to the four bit level because the eight bit resolution is too fine for meaningful run-length intonation. The abscissa values of the run length matrix are normalized so that the mean and standard deviation of the run length are the same as grey level value.

The nonspeckle area is calculated by summing the cell values in the matrix multiplied by the square of the normalized run length and dividing by the square of the corresponding grey level:

$$\text{Nonspeckle area} = (\text{Summation } P(i,j)/N*J^2/I_2) - 1$$

where P (i,j) is the element in the matrix, N is the total number of runs (this normalizes the procedure so that it is independent of the size of the region-of-interest), J is the normalized run length that corresponds to the cell, and I is the corresponding grey level. The value of "1" is subtracted to increase the dynamic range. The nonspeckle area is inversely related to marbling because it measures the predominance of long, low grey levels, which characterizes an image with low speckle and thus, low marbling.

While each of the variables discussed above relates to marbling each presents a different relationship between the pixel grey levels and marbling In order to enhance the utility of the measurement, these variables are used in a multiple regression model to develop a marbling score. In the preferred embodiment, the marbling score (MS) is formulated as: MS=17.91342+2.890843* Correlation−5643.7574 * Nonspeckle Area+13.58639 * Partial Autocorrelation. Those skilled in the art will appreciate that the coefficients of the marbling score formula can vary as the calibration set of data expands.

Figure 4B:
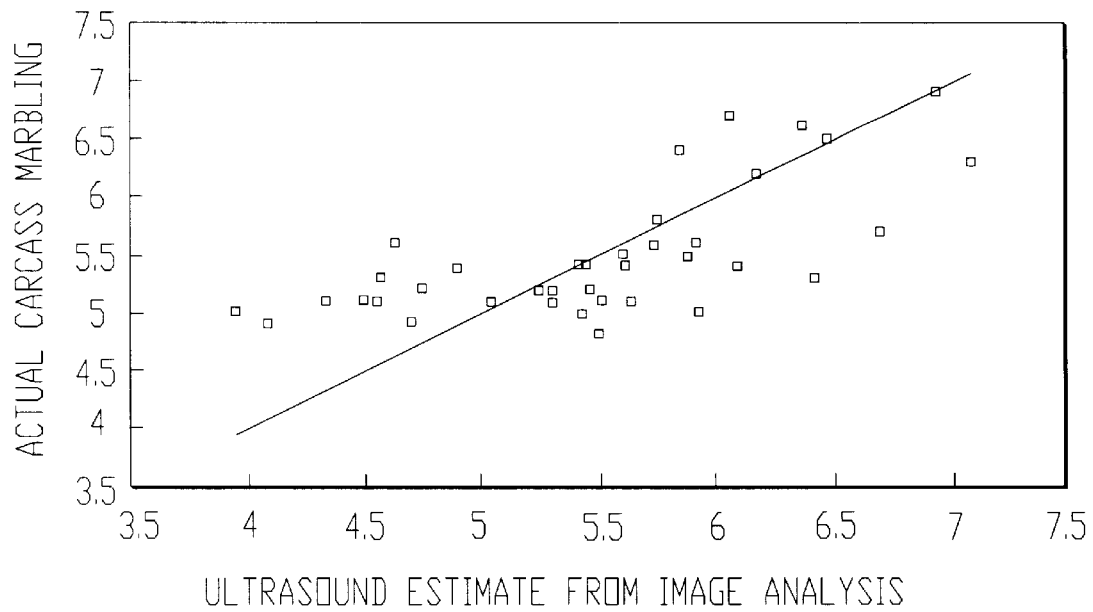
FIG. 4B is a graph representing a score of actual carcass marbling versus predicted carcass marbling using multiple regression analysis in accordance with the present invention.
Figure 4C:
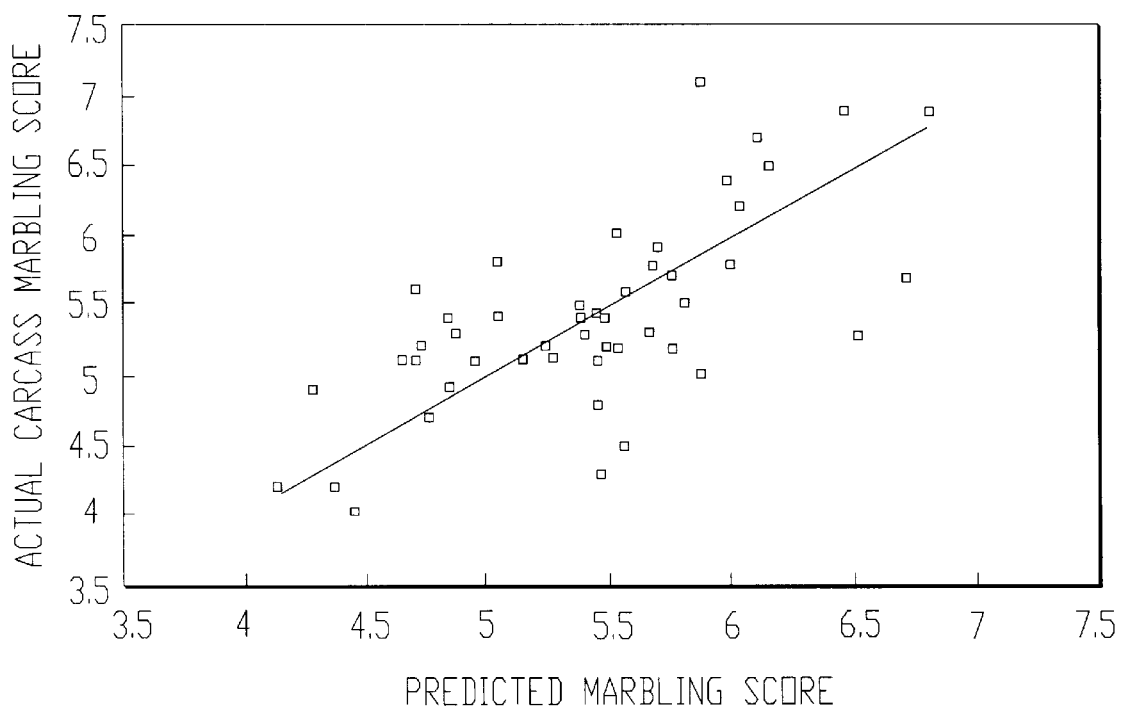
FIG. 4C is a graph representing scores of actual carcass marbling versus predicted marbling scores using neural network analysis in accordance with the present invention.

FIG. 4A is a graph of actual carcass marbling scores as determined by inspection grading after slaughter versus marbling scores (MS) developed from the ultrasound image analysis discussed above. The straight line in the graph is the isopleth line for perfect correspondence. As illustrated the average deviation from isopleth is 0.43. In another embodiment of the present invention neural computing software such as Neuralworks Explorer by NeuralWare of Pittsburgh, Pa., was used to process the three marbling variables discussed above to develop a neural network score (NNS). This software was used in place of the marbling score (MS) formula. The results of this analysis are shown in FIG. 4C which is a graph of actual carcass marbling scores versus the neural network score. As illustrated the average isopleth deviation is 0.27.

As those skilled in the art will appreciate, the present invention encompasses many variations in the preferred embodiments described herein. For example, the output from ultrasound device 12 can be provided directly to computer 16 thereby eliminating the need for VCR 14. Additionally, each of the three marbling variables provide an independent measure of marbling from the ultrasound image and could be used singly or in combination with two in some circumstances. In addition, other techniques can be developed for developing marbling scores from the image texture variables.

Livestock Disposition Apparatus and Method

Figure 5:
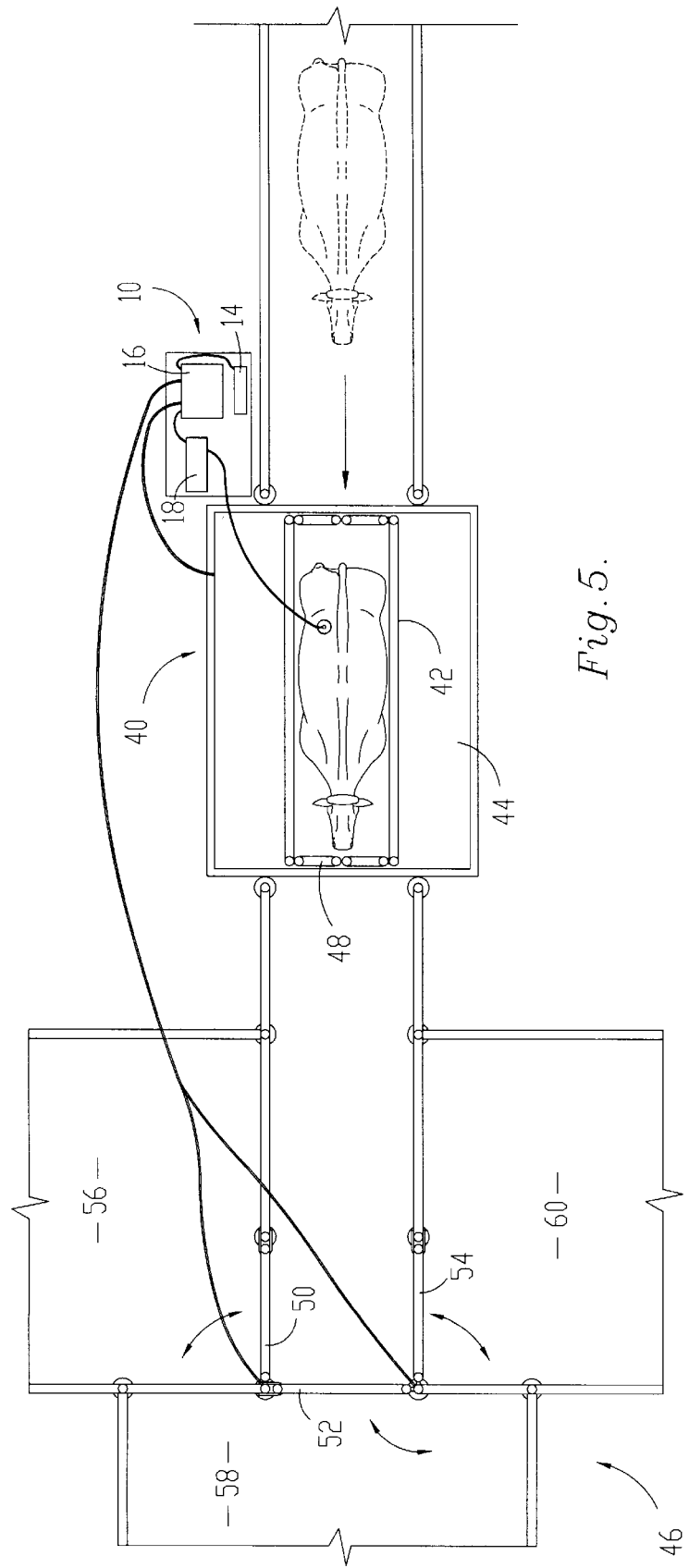
FIG. 5 is a plan view of another aspect of the invention showing a livestock chute and computer controllable gates for routing livestock to selected pens.

FIGS. 5 and 6 illustrate the preferred apparatus for embodiment 40 of the present invention for determining and controlling the disposition of livestock. In general, embodiment 40 determines the future disposition of livestock such as for sale or retention for breeding using current attribute values including marbling score, backfat thickness and live weight. Based upon the current attribute values, predicted attribute values are determined which correspond to quality grade, yield grades and carcass weight. With this information along with current and future feed costs and livestock prices, the profitability of an animal can be determined at a selected day in the future.

In the preferred embodiment, the profitability for each of the next 200 days is determined and then the highest profitability day selected as the optimal number of days on feed for maximum profitability. Animals for which the optimal days on feed fall within a select range are assigned to outcome groups. Based upon this assignment, the preferred apparatus controls the appropriate feed lot gates to route the animal to its assigned outcome group.

Referring to FIGS. 5 and 6, embodiment 40 includes apparatus 10 (FIG. 1), livestock squeeze chute 42, scale 44 and livestock containment array 46 which includes computer controllable, powered gates 48, 50, 52 and 54 with gate 48 leading from chute 42, gate 50 leading to pen 56, gate 52 leading to pen 58 and gate 54 leading to pen 60. As discussed above in connection with FIG. 1, apparatus 10 includes ultrasound device 12 for providing an ultrasonic scan output to computer 16. Scale 44 is a conventional livestock scale located under chute 42 for providing an output representative of the livestock weight to computer 16. Gates 48–54 are conventionally powered with electrical or hydraulic motors or cylinders and controlled for opening and closing by computer 16 for routing an animal in chute 42 to a selected pen 56–60.

In operations a head of livestock is placed in chute 42 where ultrasound device 12 is used to produce an ultrasonic scan output to computer 16 as discussed above in connection with FIG. 1 While still in chute 42, the livestock head is also weighed by a scale 44 and the weight thereof provided to computer 16 along with the identification number of the animal.

Figure 7:
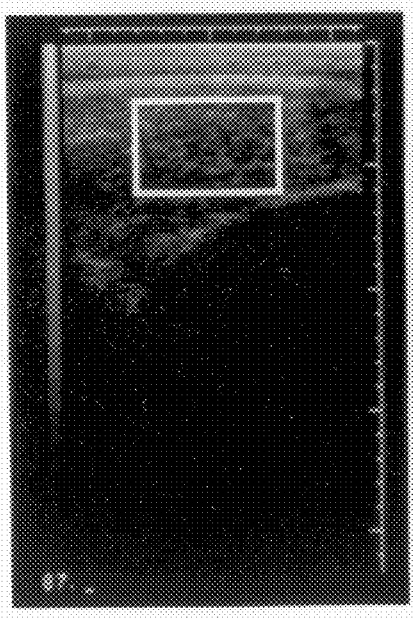
FIG. 7 is a photographic illustration of an ultrasonic echogram illustrating other aspects of the invention for determining backfat thickness and the region-of-interest for a marbling score.

Computer 16 then performs an analysis of the ultrasonic echogram received from ultrasound device 12 such as that illustrated in FIGS. 2, 3, and 7 to determine automatically a current marbling score representative of the marbling in the muscle region. Computer 16 analyzes the echogram to determine current backfat thickness as discussed herein in connection with FIG. 7 and receives the current weight of the livestock from scale 44. Computer 16 is operated in accordance with the program illustrated in the microfiche appendix incorporated herein as part of the disclosure.

Marbling score, backfat thickness and live weight are attribute values provided as inputs to computer 16. Other inputs include current and projected feed costs and livestock prices and, for a given herd, the breed (e.g., Hereford, Angus or mixed) and age (e.g., calf or yearling) of livestock being handled and the desired number of outcome groups for the herd being processed. The livestock prices also include the schedule of premiums and discounts for quality grade (e.g., prime, choice, select or standard), yield grade (e.g., YG#2) and carcass weight.

In order to determine the future profitability of the livestock head, computer 16, in accordance with the program, constructs three arrays for each of the next 200 days on feed. The first is an array of probability weighted predicted marbling scores mapped to the discount or premium for the corresponding quality grade. The second array is probability weighted, predicted backfat thicknesses mapped to corresponding discounts for yield grade. The third array is probability weighted, predicted carcass weights mapped to corresponding carcass weight discounts.

Marbling Array

The first step in constructing the marbling array is to determine a predicted marbling score as a function of the current marbling score of the head of livestock as determined by visual inspection of the ultrasound echogram or by computer controlled analysis thereof, which is preferred. The predicted or future marbling score is determined from the equation $$FMS = CMS + KD$$

where FMS is the future marbling score, CMS is the current marbling score, k is the rate coefficient and D is the number of days into the future. In the preferred embodiment, k has been derived empirically as 0.12 for calves and 0.15 for yearlings. It has been found that marbling increases with days on feed in a feedlot and the coefficient k is a factor representing the increase in the marbling score over time in days D.

It has also been found that the marbling coefficient k varies, which injects a source of error into the predicted marbling score. This variability in k may stem from errors in establishing the initial marbling score variation in individual animal growth and development, errors in the prediction function of the equation itself, and error in the final carcass grading which is a subjective process conducted by visual inspection. The error deviation of k follows a Gaussian curve corresponding to the probability of the future marbling score falling within a range according to a probability function. This probability function has been empirically derived between −2 and +2 standard deviations as $$P = 0.037553 + 22.913290*Z - 178.017972*Z^2 + 466.572554*Z^3 - 412.8737Z^4$$

where P is the cumulative area under the curve and $$Z = 1/(1 + EXP 0.436*S)$$

where S is the standard deviation at a marbling range boundary. Finally $$S = (0.000324*(EXP(3.378158 - 0.974635*LOG(D))))/k$$

where D is in days.

For that portion of the probability below −2 standard deviations the equation is $$P = 2.022717 + 12.092422*Z + 24.237903*Z^2 - 16.27763*Z^3.$$

For that portion of the curve above +2 standard deviations the equation is $$P = 1.006868 - 3.858338*Z + 50.87763809*Z^2 - 232.772662*Z^3$$

where $Z = 1/(1 + EXP\ 0.41*S)$ for these last two equations.

With these marbling score equations, the probability can be determined that the future marbling score will fall within a certain range. For example, using FMS=CMS+kD where FMS=5.07, CMS=3.05, k=0.015 and D=105 the following table can be developed:

TABLE I

| | Predicted Marbling Score | Dis./Prem. | Probability | Penalty |
|---|---|---|---|---|
| 1. | 0.10–1.99 | −17. | 0 | 0 |
| 2. | 1.99–2.99 | −13.33 | .0018 | −.0234 |
| 3. | 2.99–3.99 | −9.67 | .0638 | −.6169 |
| 4. | 3.99–4.495 | −6. | .1413 | −.8477 |
| 5. | 4.495–4.995 | −6. | .2504 | −1.5025 |
| 6. | 4.995–5.995 | .0 | .4456 | 0 |
| 7. | 5.995–6.995 | .0 | .0984 | 0 |
| 8. | 6.995–7.995 | .0 | .00357 | 0 |
| 9. | 7.995–8.995 | 6. | 0 | 0 |
| 10. | 8.995–10 | 6. | 0 | 0 |
| 11. | 10 + | 6. | 0 | 0 |
| Marbling Penalty Score | | | | −2.9911 |

The future marbling scores (first column) illustrated in Table I have been found to correspond to quality grades—specifically, lines 1–3 for standard, lines 4–5 for select, lines 6–8 for choice and lines 9–11 for prime. For the example of Table I, the discount (second column) for standard grade is $17/cwt, the discount for select is $6/cwt, and prime is at a premium of $6 with choice being at $0.

The penalty amount (fourth column) is derived by multiplying the probability (third column) of the marbling score falling in a given range times the corresponding quality grade premium or discount. For example, range 1 corresponds to a standard grade reflecting a discount of $17. The probability of the marbling score falling in this ranges however, is 0 and thus the calculated penalty is also 0 for this range. Ranges 2 and 3 also fall in the standard grade also bearing a discount of $17. It has been found, however, that the grading for standard experiences substantial variability. Because of this, the discount for range 2 is illustrated at $13.33 reflecting only a ⅔ likelihood that a grader will actually grade this marbling score at standard, Similarly for range 3, the discount of $9.67 is assigned reflecting the likelihood of an actual grade of standard at less than half. As a further illustration, range 5 bears the discount of $6 for select with a probability of 14.13% that the marbling score will fall in this range resulting in a probability weighted discount of $0.8477/cwt. It will be noted in Table I that range 6 has the highest probability of occurring which corresponds to choice grade bearing no discount or premium.

By adding the probability weighted discounts of column 4, a total predicted marbling penalty score is derived as a discount of $2.9911/cwt. Thus, it is predicted that on day D, this head of cattle will receive a probability weighted quality grade discount (marbling penalty score) of $2.9911. The marbling penalty score is determined for the next 200 days on feed for the head of cattle being held in chute 42.

Backfat Thickness Array

The process for determining the predicted, probability weighted backfat penalty is similar to that for the marbling array. The predicted future backfat thickness is calculated as $$FBF = CBF * EXP(kD)$$

where FBF is the future backfat thickness in millimeters, CBF is the current backfat thickness in millimeters, k is the rate coefficient for the increase in backfat and D is the number of days. The rate coefficient k has been empirically derived as 0.01. This coefficient can range, however, between 0.007 and 0.012 depending upon age, breed and animal weight.

As with the marbling coefficient, the backfat coefficient presents a variation which follows the same probability distribution described above for probability P. For backfat prediction, however, the standard deviation S has been found to be $$S = EXP(-1.888503 - 0.958604 * LOG(D))$$

Table II shown below illustrates the use of predicted backfat thickness in inches (first column) to determine a probability weighted, total backfat penalty (fourth column). For this example, yield grades #1 and #2 receive a premium of $1, yield grade #3 receives no penalty or discount and yield grade #4 receives a discount of $20.

TABLE II

| | Predicted Backfat Thickness | Dis./Prem. | Probability | Penalty |
|---|---|---|---|---|
| 1. | .01–.095 | 0 | 0 | 0 |
| 2. | .095–.195 | 0 | 0 | 0 |
| 3. | .195–.305 | 0 | .0085 | 0 |
| 4. | .305–.405 | 0 | .1907 | 0 |
| 5. | .405–.505 | –.50 | .4412 | –.2206 |
| 6. | .505–.605 | –2 | .2725 | –.545 |
| 7. | .605–.705 | –3 | .0726 | –.2178 |
| 8. | .705–.805 | –14 | .0127 | –.1778 |
| 9. | .805–1.005 | –20 | .00186 | –.038 |
| 10. | 1.005–2.005 | –25 | 0 | 0 |
| 11. | 2.005 + | –26 | 0 | 0 |
| Backfast Penalty Score | | | | –1.1988 |

The ranges of backfat thickness correspond in Table II to YG#1 for lines 1 and 2, YG#2 for lines 3,4 and ½ of line 5, YG#3 for ½of line 5, line 7, ½of line 8 and ¼ of line 9, and YG#4 for ½ of line 8, ¾ of line 9, and lines 10 and 11. An additional backfat penalty of –1 for line 6, –2 for line 7, –3 for line 8 and so forth through line 11 is added for the depression in animal performance (rate of gain and feed efficiency) when the animal switches from a growing to a fattened mode. This performance reduction has been experimentally determined to be correlated with backfat thickness. A penalty is assigned to each range corresponding to the discount for the predicted yield grade. Rather than show an actual premium, however, the discount column is normalized to a discount of 0 for yield grades #1 and #2 (instead of a $1 premium) and a deeper discount for the ranges corresponding to yield grades #3 and #4. Additionally, the discounts have been adjusted to reflect the empirically derived likelihood of a grader designating a particular yield grade to a particular backfat thickness. The sum of the penalty column yields the predicted total backfat penalty score for day D. This score is determined for each of the next 200 days on feed.

Carcass Weight Array

Future live weight is determined by multiplying the expected average daily gain (ADG) by the number of days D of interest. The ADG for the group of cattle being processed is estimated by feedlot management corresponding to the breed of livestock and age, and which also take into account current weight, previous history, management procedures and feed lot experience. Such estimates are well known to those skilled in the art. As an example, if the ADG is 3.1 and the initial weight is 950 pounds, a shrink factor of 4% is initially taken into account for a starting weight of 912 pounds The estimated live weight at 105 days would be 1237.5 pounds. As with marbling and backfat thickness coefficient, the ADG as a coefficient presents a deviation according to the probability equations P discussed above. For average daily gain, the standard deviation for ADG is $$S = ADG * EXP(1.225269 - 0.62966 * LOG(D)).$$

Table III illustrates an example of an array showing ranges of carcass weights and associated penalties. The penalties take into account the actual pricing penalty for underweight or overweight carcasses and the economic penalty for not feeding the head of livestock to a carcass weight of 900–950 (899.5–949.5) pounds. That is to say, the penalties include provision for the marginal profit of additional gain (retention for more days on feed) which depends on price and input cost relationships. This example assumes feed costs at $55/cwt, livestock prices at $70/cwt, and further uses the empirically based assumptions that carcass weight is 0.64 of live weight and a live weight gain of 1 pound results in a carcass gain of 0.75 pounds. To be more precise, the dressing weight is defined as follows:

Dressing percent=0.496301+0.00017155 Carcass Weight, or Dressing percent=0.478889+0.0001222 Live Weight.

These two estimates for dressing percent are equivalent and for a 1237.5 animal, the dressing percent would be about 63% resulting in 779.6 pounds carcass weight.

Additionally, the penalty discounts are determined in increments of 50 pounds corresponding to the carcass weight range increments. More particularly, the penalties in the array are determined by $$Y_i = d_i * (50 * (Price/0.64 - Cost/0.75)/800)$$

where $Y_i$ is the amount to adjust the ith discount entry in the array, and $d_i$ is the distance of the ith entry from the entry on line 10 which is the optimal carcass weight. "Price" is the market price/cwt of livestock and "Cost" is the total feedlot cost/cwt of live gain including feed, yardage and interest.

TABLE III

| | Future Carcass Weight | Discount | Probability | Penalty | |
|---|---|---|---|---|---|
| 1. | 100–500 | −35.27 | 0 | 0 | |
| 2. | 500–549.5 | −28.02 | 0 | 0 | |
| 3. | 549.5–599.5 | −15.77 | 0 | 0 | |
| 4. | 599.5–649.5 | −13.52 | 0 | 0 | |
| 5. | 649.5–699.5 | −11.26 | 0 | 0 | |
| 6. | 699.5–749.5 | −9.01 | .0079 | −.0712 | |
| 7. | 749.5–799.5 | −6.76 | .0791 | −.5351 | |
| 8. | 799.5–849.5 | −4.51 | .2892 | −1.3044 | |
| 9. | 849.5–899.5 | −2.25 | .3741 | −.8417 | |
| 10. | 899.5–949.5 | 0 | .2035 | 0 | |
| 11. | 949.5 + | −18 | .0461 | −.8298 | Total |
| Weight Penalty Score | | | | −3.5822 | |

As with the other two tables, the discount at each range is multiplied by the probability to reveal a probability weighted penalty for that range. The sum of the penalties yields a total weight penalty score which is determined for each of the next 200 days.

Maximum Profitability and Outcome Groups

As discussed above, each of the arrays illustrated in Tables I-III is calculated for each of the next 200 days. For each of these days, the three array penalty scores are added to produce a total penalty score which, in the example, is: −2.9911−1.1988−.8298=−5.0197 as the total penalty score for day D.

Next, embodiment 40 takes into account projected costs and prices by adjusting the total penalty score for each day by a respective adjustment factor for cost and price. This is accomplished by an equation for the cost adjustment factor (CAJ):

$$CAJ=D*(50*(\text{Present Price-Future Cost})/0.75)/800)-\text{Gainfactor}/100.$$

The term "Gainfactor" is the term "$Y_i$" from the equation above.

Similarly, the equation for the price adjustment factor (PAJ) is $$PAJ=D*(0.015625*(\text{Future Price-Present Price})).$$

The total penalty score for each day D is added by the cost adjustment factor (CAJ) and the price adjustment factor (PACT) for day D. For example, a price adjustment factor might be +3.2865 reflecting a projected increase in livestock prices, and a cost adjustment factor might be −0.1785 indicating a projection for higher costs in the future. Accumulating these factors with the penalty score in line 6 (−5.0197) results in a final score of −1.9117 (−5.0197+3.2865−0.1785).

The next step is to determine a profitability score (PS) for each day D. In the preferred embodiment, a profitability score of 100 is arbitrarily assigned to an 825 pound carcass with a quality grade of choice at yield grade #2. With this basis, the highest possible score with no penalties is 107. Thus, the profitability score is determined by $$PS=107\text{-}NPS(\text{Carcass Weight}/800)$$

In the example, the carcass weight is 779 pounds which divided by 800=0.97375. The recalculated NPS is −19117 yielding −1.8615. The resulting profitability score for day 105 is 105.1385.

A profitability score is calculated as described above for each of the next 200 days on feed and from this the day with the highest profitability score is selected as the number of days on feed for the highest profit. That is, the day on which the profitability score peaks is designated as the maximum profit day. Feeding beyond 200 days is not generally economical and so it is not necessary to calculate beyond 200 days to determine the most economical day in which to sell the livestock.

Those skilled in the art will appreciate that it is not practical to market a herd on too many different days. Accordingly, the most practical approach is to sort the herd into outcome groups in which each member of the group has a similar profitability score. Each outcome group is fed out for the same number of days and marketed on the same day. In the preferred embodiment, the feed lot management determines the number of outcome groups based upon the number of pens available, the size of the herds transportation capability and so forth. In generals it has been found that the number of outcome groups should be limited to four as a greater number provides no additional benefit of significance.

If two groups have been selected, the herd is split at the mean number of optimal days designated by the above procedure. If three groups have been selected, an early group is designated as less than 0.5 standard deviations of the means number of optimal days designated by the above procedure, a middle group at −0.5 to +0.5 standard deviations and a late group at +0.5 standard deviations. If a fourth group is desired, it is selected for less than −1.4 standard deviations.

After the groups have been defined, a new number of days on feed is determined to produce the maximum profitability for the group as a whole. The maximum profitability day for a group is determined by running the same procedure as was used for an individual animal on all the animals in their group. Each individual contributes a proportional part to the total profitability score and the best day to market is the day of peak profitability score. This procedure is necessary because many of the equations are nonlinear and arithmetic means are not satisfactory. In addition to finding the best day to market a groups the program estimates a profile of carcass attributes, i.e., percent in each quality and yield grade classification and also expected outliers in the weight groups that might be penalized.

It is not necessary to wait until all livestock in the herd has passed through chute 42 in order to determine the criteria for assignment to an outcome group. Until twelve head are processed, an estimated mean number of days is used to seed the procedure and the standard deviation for the number of days is set at 20. A usable estimate of days to slaughter is well known to those skilled in the art of feeding cattle. After 12 head are processed, actual mean and standard deviation of the group are calculated.

For example, FIG. 5 illustrates the use of three outcome groups respectively assigned to pens 56, 58 and 60. After computer 16 determines the outcome group assignment of the livestock head in chute 42, computer 16 opens chute gate 48 and also the appropriate one of gates 50, 52 or 54 for routing the livestock head to the pen corresponding to the assigned outcome group.

As those skilled in the art will appreciate, the invention provides a practical and sophisticated apparatus and method for handling livestock for maximum profitability. A livestock head enters chute 42 and the ultrasonic probe is placed thereon. The weight is automatically provided to computer 16 as is the ultrasonic scan. This information along with other information already in memory allows computer 16 to determine rapidly the disposition of the head of cattle and to route that head to the appropriate pen automatically for maximum profitability. As discussed above, computer 16 can also be configured to identify livestock with certain characteristics such as those deemed desirable for breeding. For example, all livestock that are predicted to grade high choice or prime might be designated for breeding or for special feeding for select customers. It will also be appreciated that after an outcome group has been marketed for slaughter, the actual weight and grade attributes and profitability can be compared to that predicted by the invention in order to adjust the variables and coefficients for even greater accuracy.

Backfat Thickness

As discussed above for determining livestock disposition, initial backfat thickness for a head of cattle is one of the input values. This can be estimated visually by a trained observer from the ultrasonic image. It is preferred however, that the backfat thickness be determined by computer 16 operating in accordance with the computer program shown in the microfiche appendix based upon the ultrasonic image and information provided by ultrasound device 12.

FIG. 7 illustrates ultrasound image 62 which includes horizontal gridline 64 and vertical gridline 66, each with centimeter markings. Image 62 presents null band 68 hide layer 70, backfat layer 72, logissimus muscle 74, rib bone 76, and marbling region-of-interest 78 indicated by rectangular border 80. Backfat layer 72 is bounded by upper edge 82 and lower edge 84.

As discussed above, the ultrasound image presented by ultrasound device is digitized to present an array of 512 rows by 512 columns of pixels presenting values that range from 0 (dark) to 255 (white) Image 62 presented in FIG. 7 is a portion or window of the total image from columns 1 to 512 and rows 1 to 512. Column 206 is the center of the image but column 200 is used as the center for computational ease. Image 62 presents about 2.25 pixels/mm. vertically and about 2.7 pixels/mm. horizontally according to the scale presented by gridlines 64–66.

Null band 68 presents the first point of reference in image 62 and the top of band 68 can be thought of as corresponding to the face of the ultrasonic probe. Band 68 is caused by the delay time when the electronic components of ultrasound unit 12 when switching between the transmit and receive modes. The speed of sound and tissue is about 1.5 mm./microsecond and the time delay in the electronic components is about 2.5 microseconds. Null band 68 falls in pixel rows 15–22 and serves as a starting point reference for locating and analyzing the features of interest in image 62.

The next identifiable feature is hide layer 68 shown as a dark band which is coincident with the top 82 of backfat layer 72. In order to locate this features the image is convolved with a matrix filter to eliminate noise and sharpen boundary interfaces. For examples with a 3×3 matrix, the value of the center pixel is replaced with the average value of that pixel and its eight neighbors according to the weighting factor values in each matrix location.

In the preferred embodiment, a 4×20 filter is used to find the dark chide) layer 70 and the top 82 of the backfat layer 72 at the same time. The coefficients of the rows 1 and 2 of the filter are −1/80 and are +1/80 for rows 3 and 4. The filter is first placed at row 18, column 170 and the filter values calculated for rows 18–33. Next, the row is selected in which the filter value has a value greater than 9 and larger than the value of the filter at the next row location (row 23 in the example of FIG. 7). These filter manipulations are repeated for columns 190 and 210 which identifies rows 24 and 26 respectively. The average of these three rows is taken ((23+24+26)/3=24.3) and added to 2.5 for a total of 26.8, which is the pixel location of the top 82 of the backfat layer 72. The addition of the value 2.5 is necessary to find the exact location of the top of the backfat layer within the dimensions of the filter. The use of this filter provides a maximum value on the row where there is an edge, specifically a shift from a dark to a bright zone which marks the top of the backfat layer.

The use of a 4×20 filter allows the image to be processed in blocks to provide a backfat measure over an extended length of the image (about 3 centimeters) By so doing, the accuracy of the measurement is greatly enhanced. It will be appreciated that there is some leeway in filter configuration. The preferred larger filter, however, helps to overcome noise and compensate for irregularities in tissue structure-specifically, the interfaces between hide and backfat and between backfat and muscle. The next step is to determine the location of the bottom of the backfat. In so doing, two problems are presented. First, the bottom of the backfat layer tends to be curved and the thickness of the backfat layer tends to be compressed by the hide. That is to say, the carcass backfat thickness increases slightly after the hide is removed. Furthermore, a different procedure must be used f or cattle with less than 3 mm. backfat because a distinct echo is not presented at the bottom of the layer.

To locate the bottom of the backfat layer, the 4×20 filter discussed above is placed at the row location equal to the top of the backfat layer (26.8 in the example) and column 180. The value of the filter is calculated. The result is the average of the pixel values at the two rows representing the top of the backfat layer. This value is 139.6 in the example.

Next, a 3×40 filter with all coefficients equal to 1/120 at the top of backfat pixel row plus 7 (row 36 in the example) and with the upper left cell on column 180. The value is calculated which is 124.5. This procedure is repeated for the next 55 rows to row 84 in the example. The maximum value from the 55 filter calculations is selected and 10 added to the result (189.7 in the example). This value is compared to the value using the 4×20 matrix. If greater, this indicates the backfat layer is more than 3 mm. thick.

If the backfat layer is more than 3 mm., a 6×10 filter is used with the coefficients in rows 1–3 at −1/60 and +1/60 in rows 4–6. Convolving this filter with the image searches for the top edge of the bright band that represents the bottom 84 of the backfat layer 72. Initially the filter is placed with its upper left corner at the top of the backfat layer+1 (row 30 in the example) and on column 30, and the value calculated. This is repeated for the next 50 rows to row 79. The row with the highest filter value is noted and the procedure repeated but shifting five columns to the right for the 50 rows. This continues until column 250. This provides a set of 21 row locations of maximum filter values.

The 9 highest and 6 lowest values of the 21 row locations are discarded and the remaining 6 values averaged to determine the top of the bright band representing the bottom of the backfat layer. In the example, the average value is 35.5 for the bottom 84 of the backfat layer 72. The difference between bottom 84 (35.5) and top 82 (24.3) is 11.2 pixels, or 11.2 mm. at 2.25 pixels/mm.

For thin animals with backfat thickness less than 3 mm., a different procedure is used to find the bottom of the backfat layer. A 6×10 filter is defined with the coefficients for rows 1–6 being +0.3, +0.2, +0.1, −0.2, and −0.3, respectively. The use of this filter will provide a maximum value when the descending slope is the steepest In thin cattle, the top and bottom backfat borders commingle. This filter locates the lower side of the bottom band where the plateau of high values (brightness) begins to fade away.

The filter is initially positioned at the top of the backfat layer plus 1 pixel (row 31 in the example) and on column 170. The filter values are calculated for 8 rows and the row with the maximum value noted (row 34 in the example). The filter is then shifted ten columns to the right and the procedure repeated for columns 180, 190, 200, 210, and 220 yielding six additional rows of maximum value. These six rows are averaged to determine the bottom 84 of backfat layer 72 which is 32.5 in the example. The thickness of the backfat layers is calculated as (32.5−30.03)/2.25=1.10 mm. It has been found that ultrasound measures on the live animal tend to be lower than carcass measures of backfat. It is thought that the difference results from postmortem expansion of backfat after the hide is removed. To correct for this defects the following adjustment is added to the preliminary estimate of backfat thickness:

$$\text{Adjustment}=0.5008*\text{thickness}-0.012155*\text{thickness}^2-0.2585$$

Region-of-Interest

Referring to FIG. 7, border 80 defines Region-of-Interest 78 for determining a marbling score. The Region-of-Interest is made up of twenty thousand pixel values and needs to be placed in the muscle region below backfat layer 72 but above rib bone 76. This is so the region is uniformly echoic and does not contain specular echo from either the backfat layer or the rib bone. The preferred technique for placing the Region-of-Interest locates the rib bone and places the region just above.

First, a 12×201 filter is constructed with rows 1–6 having the coefficients −$\frac{1}{2412}$ and +$\frac{1}{2412}$ for rows 7–12. The filter is placed at column 100 and at the bottom of the backfat layer (as identified above) plus 20 pixels. The filter values are calculated with the upper left corner of the filter initially at bottom +20 to bottom +120, one row at a time. If a filter value calculation yields a value greater than 10, then that row is chosen as the bottom row of the Region-of-Interest (ROI). If all of the filter values are less than or equal to 10 then the bottom of the ROI is set at bottom +118. That is, 118 pixels below the bottom of the backfat layer. This results in an ROI with the dimension of 100×201.

The procedure for locating backfat and the Region-of-Interest can be used when the ultrasonic transducer is oriented either parallel or transverse to the backbone. It should also be noted that this procedure also determines the depth of the longissimus muscle.

Determining a Marbling Score

As discussed above, a marbling score is an attribute used as an input for determining livestock disposition. The marbling score can be determined from inspection of an ultrasonic image by a trained observer. It is preferred, however, that the marbling score be determined by computer 16 based on the ultrasonic image and information provided by ultrasound device 12. As with determining backfat thickness, using computer 16 provides consistent, objective results without the need for a trained observer.

The preferred method of determining a marbling score uses a neural network procedure as set forth in the microfiche appendix incorporated herein to analyze Region-of-Interest 78. It has been found that this is superior to autoregression and correlation from a gray scale co-occurrence matrix because these, along with Fourier analysis, all measure just the wave form of the pattern.

A neural network consists of layers of nodes which correspond to synapses among nerves. In the present invention, four nodes are present in the input layer because there are four texture statistics that act as parameters of the image. These texture statistics include local standard deviation (LSTD) gray level co-occurrence homogeneity (GLCCH) run length matrix also called speckle estimator (SPEC) and the product of LSTD and SPEC.

There are also three nodes in the hidden layer that accept input from the input layer nodes. Finally, there is one node in the output layer which is the estimated marbling score. In addition, a bias node links the output node and the hidden nodes. This bias node corresponds to the constant in a simple polynomial equation.

The neural network is trained by repeatedly presenting the four textured statistics to the input nodes along with the correct outcome to the output node until the configuration is able to relate inputs with the correct marbling score. About six million iterations provide a workable solution. In the preferred embodiment, a conventional neural network program is used such as Neural Ware-Explorer Version. This allows the solution to be coded in Fortran. The number of texture statistics and the architecture of the preferred neural network are intentionally simple to provide stability during validation.

A sigmoid equation is used as a transfer function at each node. This allows for non-linearity in data sets. The following is a description of the method steps embodied in more detail in the program of the microfiche appendix.

Step 1: Normalize each pixel vector of the Region-of-Interest 78 for interlacing effects that can result from inadequate synchronization of the digitizing board and the ultrasound output signal. This can be a particular problem when images are transported from the ultrasound device to the digitizing board using conventional VCR tape. It is preferred to capture images directly from the analog port of the Aloka 210 Ultrasound System to a PIP-512B Video Digitizer Board available from Hatrox Electronic Systems, Dorval, Quebec, Canada. This board can be used with Fortran code for compatibility. The images can be windowed and are stored in binary format which are converted to ASCII for numerical analysis. With these procedures the interlacing is sufficiently minimized. The calculations are performed on the pixel row vectors and the pixel value array correspond to the axial direction of the ultrasound beam. The normalization procedure adjusts each row vector to a mean pixel value of 100.

Step 2: Delete the first five columns at the top of the Region-of-Interest 78 to ensure that no noise from the bottom of the backfat layer is present. A sagittal scan (parallel to the backbone) also helps minimize reverberation artifact effects.

Step 3: Calculate the local standard deviation (LSTD) In this procedure, an 11×1 window (or primitive) is run across every row of the pixel array making up Region-of-Interest 78 and the standard deviation within each window is calculated and accumulated for averaging. The LSTD is a measure of the "jaggedness" of the patterns and presents a high negative correlation with marbling.

Step 4: Adjust for attenuation with regression analysis. This procedure levels the pixel values in the image. Attenuation differences are unavoidable consequences of the insonating environment because variations in hair coat, temperature, backfat thickness and so forth interfere with signal energy. The adjustment in this step minimizes the effects of these variations.

Step 5: Build the 20th neighbor gray level co-occurrence matrix from the axial vector. This is an array of matched pairs of pixels spaced 20 units apart and mapped according to gray level values.

Step 6: Calculate the homogeneity of the co-occurrence matrix. This is basically the average of the squared entities in the co-occurrence matrix. It is a Markovian statistic that emphasizes paired values that repeat and using the 20th neighbor gives it a global interpretation. This statistic is positively correlated with marbling and related to texture that is uniform over the entire ROI 78.

Step 7: Rectify the array from 8 bits to 4 bits for 16 gray levels. This results in a run length array that is useful. It has been found that a resolution of 256 gray levels is too fine to obtain run lengths that can indicate texture.

Step 8: Build a gray level, run length array similar to the co-occurrence matrix discussed above but with rows representing gray levels and columns representing run lengths.

Step 9: Normalize the array of Step 8 so that the run lengths and gray levels have the same standard deviation.

Step 10: Calculate the speckle estimator (SPEC) which is the emphasis on run length divided by gray level emphasis. The distributions in this array are clustered so that they are not responsive to conventional Harkovian measures. The quadrant emphasis measures interpret this information. In other words, the speckle estimator measures regions of darkness in the image as discussed above. SPEC is negatively correlated with marbling.

Step 11: Process the texture statistics in the neural network configuration.

Step 11A: Normalize the four texture statistics so that the values range between 0 and 1. This is conventional in neural network applications. The following four equations normalize the inputs where PE1 is the bias node, PE2–5 are the input nodes, PE6–8 are the three hidden nodes and PE9 is the output nodes:

$$PE2=(SPEC-0.000398)/(0.001015-000398)$$

$$PE3=(GLCC-0.000209)/(0.000781-000209)$$

$$PE4=(LSTD-10.6562)/(18.2381-10.6562)$$

$$PE5=(LSTD*SPEC-0.00433)/(0.01851-0.00433)$$

Step 11B: Calculate the values transferring from the four input nodes to the three hidden nodes. The constant in these equations is the value from the bias nodes. The other coefficients result from training the neural net and change with accumulation of data sets for the training process.

$$PE6=0.265205-0.268740*PE2-4.388980*PE3+1.132660*PE4+0.54886*PE5$$

$$PE7=4.744430+4.0185168*PE2+1.1993338*PE3+0.825696*PE4+4.112259*PE5$$

$$PE8=0.943517+7.103221*PE2+2.424662*PE3+0.913319*PE4+3.684031*PE5$$

Step 11C: Use a sigmoid transfer function to process the inputs to the hidden nodes. A sigmoid function is preferred but it will be appreciated that other functions can be used such as sine tangent and linear. The transfer functions aid in the ability of the network to accommodate non-linearity and to dampen odd input data.

$$PE6=1/(1+e^{**}(-1*PE6))$$

$$PE7=1/(1+e^{**}(-1*PE7))$$

$$PE8=1/(1+e^{**}(-1*PE8))$$

Step 11D: Gather the output from hidden nodes, apply appropriate weights and transform with the transform function. The final value for PE9 is a normalized predicted marbling score.

$$PE9=3.382251+1.950193*PE6-1.878543*PE7-4.514792*PE8$$

$$PE9=1/(1+e^{**}(-1*PE9))$$

Step 11C: Convert the normalized output to a real marbling score. The software normalizes the outputs to a range of 0.2–0.8 instead of 0–1.0.

$$MARB=(PE9-0.2)0.6*(8.3-3.8)+3.8$$

It will be appreciated that the equations set forth above from the neural network do not have stable coefficients. During the training procedure, weights are adjusted in a random manner so that the output is not repeated. Additional training iterations results in different coefficients with increasing stability. Additionally, the equations set forth above are the results of training with images taken with a sagittal orientation A separate and distinct training session would be needed for scans transverse to the backbone.

Having thus described the preferred embodiment of the present inventions the following is claimed as new and desired to be secured by Letters Patent:

I claim:

1. A method of determining the disposition of livestock comprising the steps of:

(a) after the performance of an ultrasonic scan on a selected muscle region of a head of livestock, receiving in a computer a plurality of initial attribute values produced as a result of the ultrasonic scan and representative of attributes of the muscle region at the time of the ultrasonic scan;

(b) using said initial attribute values in said computer to predict what said attribute values will be, as predicted future attribute values at an identifiable time in the future, said identifiable time in the future being a plurality of days after said performance of said ultrasonic scan and sufficient to make said initial attribute values subject to change; and (c) using said predicted future attribute values in determining the profitability of maintaining the head of livestock on feed until said identifiable time.

2. The method as set forth in claim 1, before step (a), performing said ultrasonic scan and producing said attribute values.

3. The method as set forth in claim 2, said performing step including the step of scanning the region of the longissimus dorsi muscle and adjacent backfat.

4. The method as set forth in claim 1, said attribute values including a marbling score representative of marbling in the muscle region.

5. The method as set forth in claim 1, said attribute values including backfat thickness.

6. The method as set forth in claim 1, said attribute values including the weight of the livestock.

7. The method as set forth in claim 1, step (c) including the step of determining the projected relative profit upon sale of the livestock for slaughter after a specified number of days on feed.

8. The method as set forth in claim 1, step (c) including the step of determining the number of days on feed for the livestock for maximum profitability upon sale for slaughter.

9. The method as set forth in claim 1, step (b) including the step of determining a set of probabilities for said predicted attribute values.

10. The method as set forth in claim 9, further including the step of determining said predicted attribute values weighted according to said probabilities.

11. The method as set forth in claim 10, said attribute values including a marbling score representative of marbling in the muscle region, backfat thickness in the muscle region and the weight of the livestock.

12. The method as set forth in claim 11, further including the step of correlating said marbling score with quality grade, said backfat thickness with yield grade and said livestock weight with carcass weight.

13. The method as set forth in claim 1, step (c) including the step of determining the assignment of each head of livestock to a group having said predicted attribute values within a specified range.

14. The method as set forth in claim 1, step (c) including the step of determining whether the livestock should be bred according to the said predicted attribute values.

15. The method as set forth in claim 1, step (c) including the step of determining whether to feed the head of livestock for a number of days according to said predicted attribute values.

16. The method as set forth in claim 15, further including the step of determining the optimal number of days on feed for maximum profitability.

17. The method as set forth in claim 16, further including the step of assigning the head of livestock to a group having said optimal number of days on feed within a specified range.

18. The method as set forth in claim 17, further including the step of determining the optimal number of days on feed for said group for maximum of profitability of said group.

19. The method as set forth in claim 1, before step (a) holding the head of livestock in a livestock holding area associated with a plurality of pens until completion of step (c) and then routing the head of livestock to a specified pen determined in accordance with said predicted attribute values.

20. The method as set forth in claim 19, there being a plurality of computer controllable gates for said routing, said method including the step of using said computer to control said gates for said routing.

21. The method as set forth in claim 19, said holding area including means for weighing the head of livestock, said method including the step of providing the weight of the livestock to said add of computer as said attribute values.

22. The method as set forth in claim 19, further including the step of performing said ultrasonic scan on the livestock while in said holding area.

23. The method as set forth in claim 19, said holding area including means for weighing the head of livestock, said method further including the steps of providing the weight of the livestock to said computer as one of said attribute values, and providing a marbling score representative of marbling in the muscle region and backfat thickness resulting from said ultrasonic scan as attribute values.

24. The method as set forth in claim 23, further including the step of determining at least one of said marbling score and backfat thickness based upon a visual inspection of an ultrasonic image resulting from said ultrasonic scan.

25. The method as set forth in claim 23, further including the step of determining at least one of said marbling score and backfat thickness based upon computer processing of said ultrasonic scan.

26. The method as set forth in claim 1, further including the steps of:

before step (a), performing said ultrasonic scan and weighing the head of livestock in a holding area, analyzing said ultrasonic scan in the computer to produce a marbling score representative of marbling in the muscle region and to determine backfat thickness, receiving the weight of the head of livestock in the computer, said attribute values, including said marbling score, backfat thickness, and weight, step (c) including the step of using said predicted attribute values to determine the optimal number of days on feed for maximum profitability of the head of livestock.

27. The method as set forth in claim 26, step (c) including the step of using the cost of feed and livestock prices in determining said days on feed.

28. The method as set forth in claim 27, further including the step of using projected cost of feed and livestock prices in determining said days on feed.

29. The method as set forth in claim 26, said holding area being associated with a plurality of livestock pens, said method further including the steps of holding the head of livestock in said holding area until completion of step (c) and then routing the head of livestock to a specified pen determined in accordance with said predicted attribute values, there being a plurality of computer controllable gates for said routing, said method including the step of using said computer to control said gates for said routing.

30. The method as set forth in claim 29, further including the steps of assigning the head of livestock to a group having said optimal number of days on feed within a specified range and assigning said group to said specified pen.

31. An apparatus for determining the disposition of livestock comprising:

computer means; and means for receiving into said computer means a plurality of initial attribute values produced at least in part as a result of an ultrasonic scan on a selected muscle region of a head of livestock, said ultrasonic scan being representative of at least one of said attributes of a muscle region at the time of the ultrasonic scan, said computer means including means for producing from said initial attribute values predicted future attribute values representative of said attributes at an identifiable time in the future, said identifiable time in the future being a plurality of days after said ultrasonic scan and sufficient to make said initial attribute values subject to change, and for using said predicted future attribute values for determining the disposition of the head of livestock.

32. The apparatus as set forth in claim 31, said attribute values including at least one of a marbling score representative of marbling in the muscle region, backfat thickness, and the live weight of the head of livestock, said attribute values respectively corresponding to the attributes of quality grade, yield grade, and carcass weight.

33. The apparatus as set forth in claim 32, said disposition including the number of days on feed for the head of livestock.

34. The apparatus as set forth in claim 33, said disposition including the number of days on feed for the head of livestock for maximum profitability upon sale for slaughter.

35. The apparatus as set forth in claim 34, said computer means including means for determining said disposition further on the basis of feed costs and livestock prices.

36. The apparatus as set forth in claim 35, said computer means including means for determining said disposition further on the basis of projected feed costs and livestock prices.

37. The apparatus as set forth in claim 36, said computer means including means for assigning the head of livestock to a group associated with a specified range of days on feed.

38. The apparatus as set forth in claim 37, said computer means including means for determining the optimal days on feed for said group for maximum profitability of said group.

39. The apparatus as set forth in claim 1, said computer means including means for assigning the head of livestock to a group associated with a specified range of said predicted attribute value.

40. The apparatus as set forth in claim 39, there being a plurality of pens for holding livestock and means for routing livestock to a selected pen by way of computer means controllable gates, said computer means including means for controlling said gates for routing the head of livestock to a pen assigned to said group.

41. An apparatus for determining the disposition of livestock comprising:

means for weighing a head of livestock in a holding area and for providing a weight output representative of the weight thereof;

means for producing an ultrasonic scan on a selected muscle region of the head of livestock and for providing a scan output representative of said scan;

a computer means; and means for receiving into said computer means said scan output and said weight output, said computer means including means for responding to said scan and weight outputs for producing a plurality of initial attribute values including a marbling score representative of marbling in the muscle region, backfat thickness and live weight of the head of livestock respectively corresponding to the attributes of quality grade, yield grade and carcass weight, said computer means including means for predicting what said initial attribute values will be predicted attribute values at an identifiable time in the future and for using said predicted attribute values for determining the optimal days on feed for maximum profitability upon sale of the head of livestock, and including means for assigning the head of livestock to a group associated with a specified range of profitability, there being a plurality of pens associated with the holding area for holding livestock and means for routing livestock to a selected pen by way of computer means controllable gates, said computer means including means for controlling said gates for rotting the head of livestock to a pan assigned to said group.

42. The apparatus as set forth in claim 41, said computer means including means for determining the optimal days on feed for said group for maximum profitability of said group.

43. A method of determining the disposition of livestock comprising the steps of:

generating for a head of livestock a plurality of initial attribute values representative of attributes of the head of livestock at the time of generation of said initial attribute values, said generating step including the step of performing an ultrasonic scan on a selected muscle region of said head of livestock with at least one of said initial attribute values being derived from said ultrasonic scan;

receiving said initial attribute values in a computer, and using said initial attribute values in said computer to predict what said attributes of said head of livestock will be as predicted future attributes, at an identifiable time in the future, said identifiable time in the future being a plurality of days after said performance of said ultrasonic scan and sufficient to make said attributes subject to change; and using said predicted future attributes in determining the profitability of maintaining said head of livestock on feed until said identifiable time.

44. The method of claim 43, at least two of said attribute values being derived from said ultrasonic scan.

* * * * *

UNITED STATES PATENT AND TRADEMARK OFFICE
CERTIFICATE OF CORRECTION

PATENT NO. : 5,960,105
DATED : 09/28/1999
INVENTOR(S) : John Brethour

It is certified that error appears in the above-identified patent and that said Letters Patent is hereby corrected as shown below:

In column 2, line 24, please amend "Fig. 2A" by changing the designation thereof to --Fig. 2--.
In column 2, lines 26-27, please delete "Fig. 2B is a photographic illustration of an ultrasonic echogram correlated with a grade of USDA Low Select;".
In column 3, line 34, please delete"FIGS. 2B and 3B are" and substitute therefore --FIG. 3B is--.
In column 3, line 35, please delete "images" and substitute therefore --image--.
In column 3, lines 36-37, please delete "these images" and substitute therefore --this image--.
In column 3, line 37, please delete "FIG. 1" and substitute therefore --FIG. 6--.
In column 3, please delete lines 46-49 and substitute therefore --muscle 28 in FIG. 3B--.

Signed and Sealed this

Twenty-seventh Day of June, 2000

Q. TODD DICKINSON

*Attest:*

*Attesting Officer*          Director of Patents and Trademarks